United States Patent
Marsala et al.

[11] Patent Number: 5,844,136
[45] Date of Patent: Dec. 1, 1998

[54] DEVICE FOR MEASURING THE PERMEABILITY OF ROCK FRAGMENTS

[75] Inventors: Alberto Marsala, Bergamo; Marco Brignoli, Brugherio; Frederic Santarelli, S. Donato Milanese; Adriano Figoni, Orio Litta; Elio Rossi, Lodi, all of Italy

[73] Assignee: Agip S.p.A., Milan, Italy

[21] Appl. No.: 781,292

[22] Filed: Jan. 13, 1997

[30] Foreign Application Priority Data

Jan. 24, 1996 [IT] Italy .................................. MI96A0111

[51] Int. Cl.⁶ ........................................................ G01N 15/08
[52] U.S. Cl. ............................................. 73/38; 73/152.05
[58] Field of Search ................................ 73/38, 152.05, 73/152.09, 152.11, 152.07

[56] References Cited

U.S. PATENT DOCUMENTS

| | | | |
|---|---|---|---|
| 2,662,401 | 12/1953 | Florent . | |
| 4,555,934 | 12/1985 | Freeman et al. . | |
| 4,608,859 | 9/1986 | Rockley | 73/153 |
| 5,069,065 | 12/1991 | Sprunt et al. | 73/153 |
| 5,109,398 | 4/1992 | Hunt et al. | 378/208 |
| 5,241,859 | 9/1993 | Smith . | |
| 5,285,692 | 2/1994 | Steiger et al. . | |
| 5,299,453 | 4/1994 | Sprunt et al. | 73/153 |
| 5,311,766 | 5/1994 | Persoff et al. | 73/38 |
| 5,503,001 | 4/1996 | Wong | 73/38 |
| 5,544,520 | 8/1996 | Graf et al. . | |

*Primary Examiner*—Hezron E. Williams
*Assistant Examiner*—Jay L. Politzer
*Attorney, Agent, or Firm*—Nikaido Marmelstein Murray & Oram LLP

[57] ABSTRACT

The present invention relates to a device used for the direct measurement of the permeability of rock fragments coming directly from the drilling of an oil well and commonly called cuttings, consisting of a hollow cylindrical body (c) that presents an inlet hole for the fluid (i), a thread for closing it (h) and a hydraulic seal (g) in which is placed the sample holder disk (d) which rests on the seal (g) and is overlapped by a porous sintered steel septum (e) on which a closing plug (f) is situated with an outlet hole for the fluid (i') and the same is also provided with a thread (h') to enable it to close on the body (c).

The device can be used to obtain, directly on site, the measurement of permeability along the whole length of an oil well.

8 Claims, 5 Drawing Sheets

DEVICE FOR MEASURING THE PERMEABILITY OF ROCK FRAGMENTS

The present invention relates to a device used for the direct measurement of the permeability of rock fragments coming directly from the drilling of an oil well and commonly called cuttings, consisting of a hollow cylindrical body (c) that presents an inlet hole for the fluid (i), a thread for closing it (h) and a hydraulic seal (g) in which is placed the sample holder disk (d) which rests on the seal (g) and is overlapped by a porous sintered steel septum (e) on which a closing plug (f) is situated with an outlet hole for the fluid (i') and the same is also provided with a thread (h') to enable it to close on the body (c).

The device can be used to obtain, directly on site, the measurement of permeability along the whole length of an oil well.

The sample holder disk (d) is shown in FIG. 1 and constitutes another part of this invention.

Determination of the permeability of rocks involved in drilling and oil production, constitutes an essential part of the activity known as "Formation Evaluation" carried out by all oil companies.

Amongst those measurements carried out in the laboratory on samples of rock taken from cores for petrophysical characterisation, the determination of permeability is fundamental; in fact this carrying property defines the capacity of a material (rock for example) to allow one or more fluids (e.g. water, gas or oil) to pass through it.

At present, direct measurement of permeability is only possible on samples of rock taken from a test core; the main limits of this method such as times (considerable, because the core must be obtained and samples sent to a laboratory for analysis) and costs (connected, above all, with the withdrawal of the test core itself and which can be incurred only for samples coming from the so called "pay zones" and certainly not for the entire length of the oil well) mean that permeability is known only for the sections of a well that have been cored and only a long time after the drilling operations.

In order to find solutions to these considerable limitations and to establish the permeability of rock formations, it has been developed several semi-empirical correlations between permeability and other petrophysical properties such as porosity, clay content, speed of sound waves, electrical measurements etc. determinable by probes inserted into the oil well (logs); this indirect method of determining permeability, even if requires difficult calibration operations depending on the lithology in question, it is, at present, the only method available in those parts of the well from which cores have not been taken but, having at times no clear physical meaning, it is in any case far from being as reliable as direct measurement.

The Applicant has now developed a device that, by direct determination of permeability on cuttings, provides fundamental information on the nature of the rock strata crossed during drilling, so that fast actions can be taken if necessary.

This invention therefore relates to a device used for the direct measurement of the permeability of rock fragments coming directly from the drilling of an oil well and commonly called cuttings, consisting of a hollow cylindrical body (c) that presents an inlet hole for the fluid (i), a thread for closing it (h) and a hydraulic seal (g) in which is placed the sample holder disk (d) which rests on the seal (g) and is overlapped by a porous sintered steel septum (e) on which a closing plug (f) is situated with an outlet hole for the fluid (i') and the same is also provided with a thread (h') to enable it to close on the body (c).

The purpose of this invention is to obtain, directly on site, the measurement of permeability along the whole length of an oil well.

Figure 1:
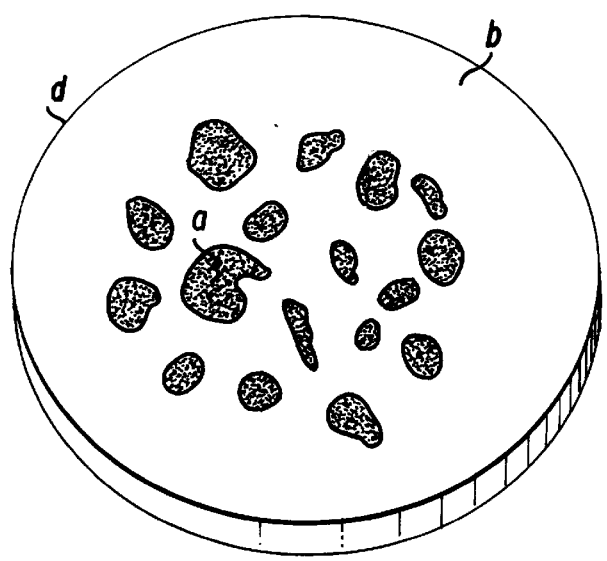
FIG. 1 illustrates a sample holder disc according to the present invention.

The sample holder disk (d) used by the Applicant to measure permeability thorugh rock fragments, is shown in FIG. 1 and also constitutes a further part of this invention.

It consists of a resin (b), initially placed in its liquid state in a circular mould, in which the cuttings (a) are encapsulated; after the resin has hardened, the disk is ground so that its faces are flat and parallel and so that the two surfaces of each encapsulated cutting are exposed on each side of the disk.

Particular care must be taken in choosing the resin (b), which must have the following properties:

non-aggressive even for highly permeable cuttings;

non-toxic for use on site;

easy to prepare and with a high degree of homogeneity;

hardening with fast setting time at atmospheric pressure and without the production of excessive heat which might modify the properties of the cuttings;

high rigidity after setting;

easy to cut and to grind;

optically opaque to permit the determination of the exposed surfaces of rocks.

Particularly, the resin (b) is chosen among epoxy, polyurethane or acrylic resins.

Figure 8:
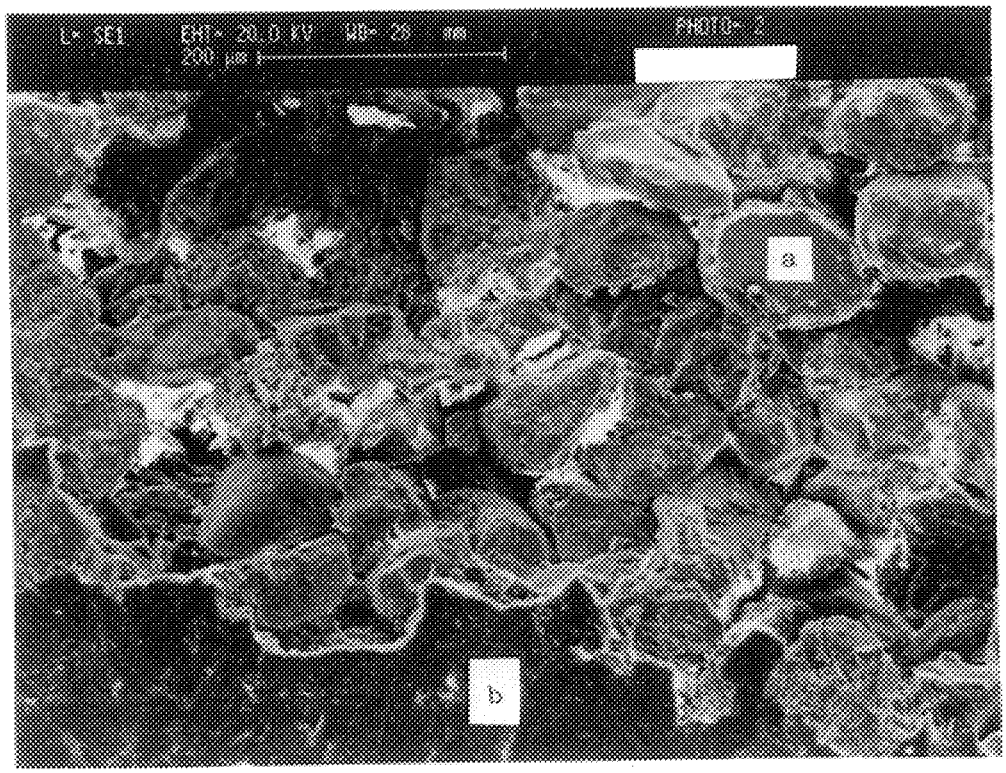
FIG. 8 is a photograph of a sample holder disc of the present invention as viewed through an SEM Microscope.

FIG. 8 shows a photograph of the detail sample holder disk realized by an Scanning Electron Microscope (SEM) in which it can be seen that the resin (b) does not penetrate inside the porous matrix of the cutting (a) even with highly permeable samples (the photograph in question is of a sandstone of 530 millidarcy (mD).

Figure 2:
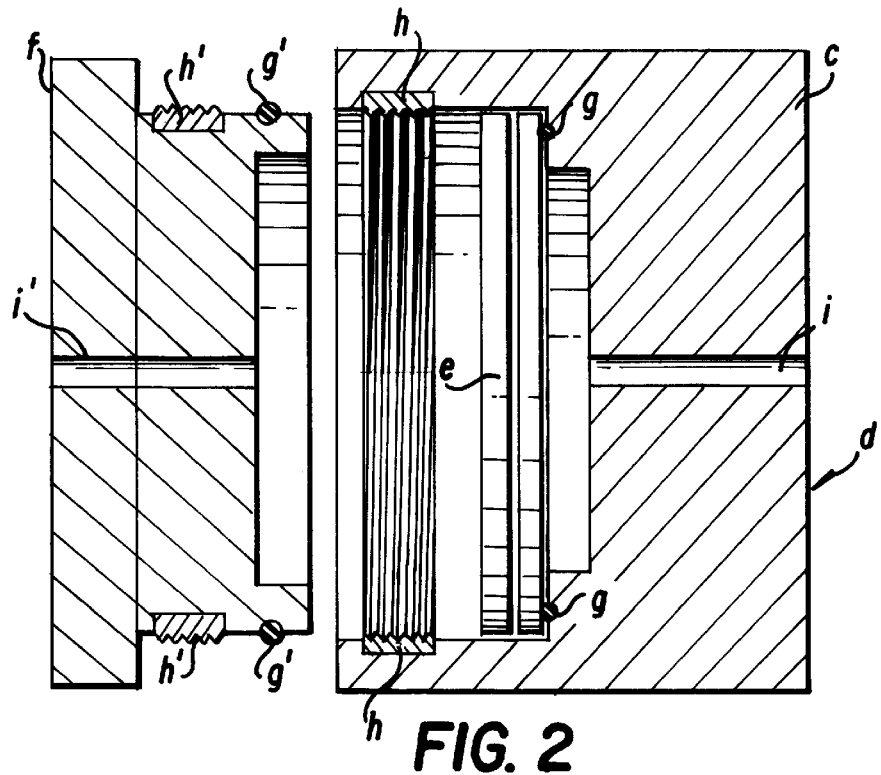
FIG. 2 illustrates a cross section of a device according to the invention.

FIG. 2 shows a cross section of the device object of this invention: it consists of a hollow cylindrical body (c) that presents an inlet hole for the fluid (i), a thread for closing it (h) and a hydraulic seal (g) in which is placed the sample holder disk (d) which rests on the seal (g) and is overlapped by a porous sintered steel septum (e) on which a closing plug (f) is situated with an outlet hole for the fluid (i') and the same is also provided with a thread (h') to enable it to close on the body (c).

In particular, the porous septum (e) is used to prevent the sample holder disk (d) from bending and breaking.

Figure 3:
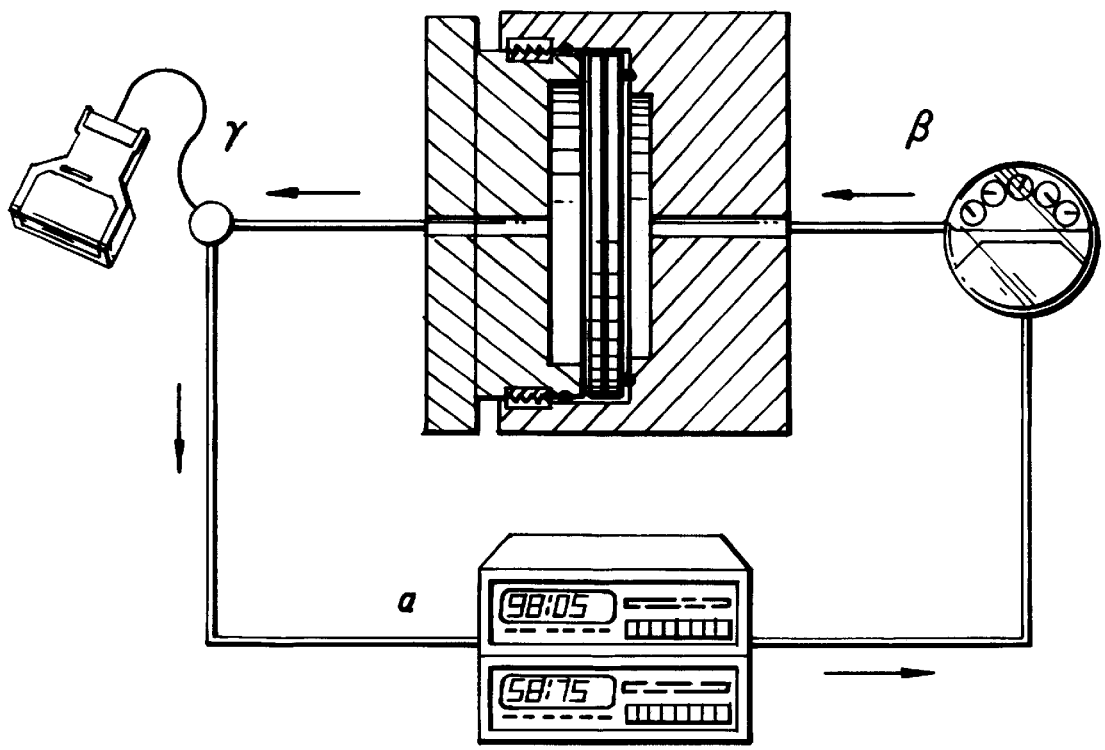
FIG. 3 illustrates a hydraulic circuit used for measurement.

Only for the purpose of illustrating the invention and without being in any way limitative of the invention itself, FIG. 3 shows a diagram of the hydraulic circuit used for measurement: it consists of a pump (α) which ensures a pressure difference between the two faces of the disk (d), measured by a manometer (β), while the flow rate of the fluid employed for the measurement is provided by a flowmeter (γ).

Experiments are carried out as follows: the sample holder disk (d) is prepared as described above and, after grounding, the surface area of the exposed cuttings on the two faces of the disk itself is calculated using transparent millimeter graph paper or a video camera and image recognition software that will calculate the area for the flow semi-automatically.

The disk (d) is then inserted in the measuring device, object of this invention, allowing the passage of the fluid to be tested through the cuttings encapsulated in it; creating pressure differences between the two faces of the disk by the pump (α), the corresponding flow rates of the fluid are measured using the flowmeter (γ) and such values, inserted in the Darcy equation, permit to determine the hydraulic permeability (steady state method).

It is also possible to perform a non steady state flow test in the same way by employing the pump (α) to create a pressure difference between the two faces of the disk (d) and by measuring the time required to reach the equilibrium.

The device, object of this invention, therefore uses said resin disks, allowing direct measurement of permeability on cuttings as it is done on samples taken from a test core.

The Applicant, without any limitation to the content of this invention, has constructed devices with the body both in steel and plexiglas with which a series of measurements were made to demonstrate the feasibility of the method.

Figure 4:
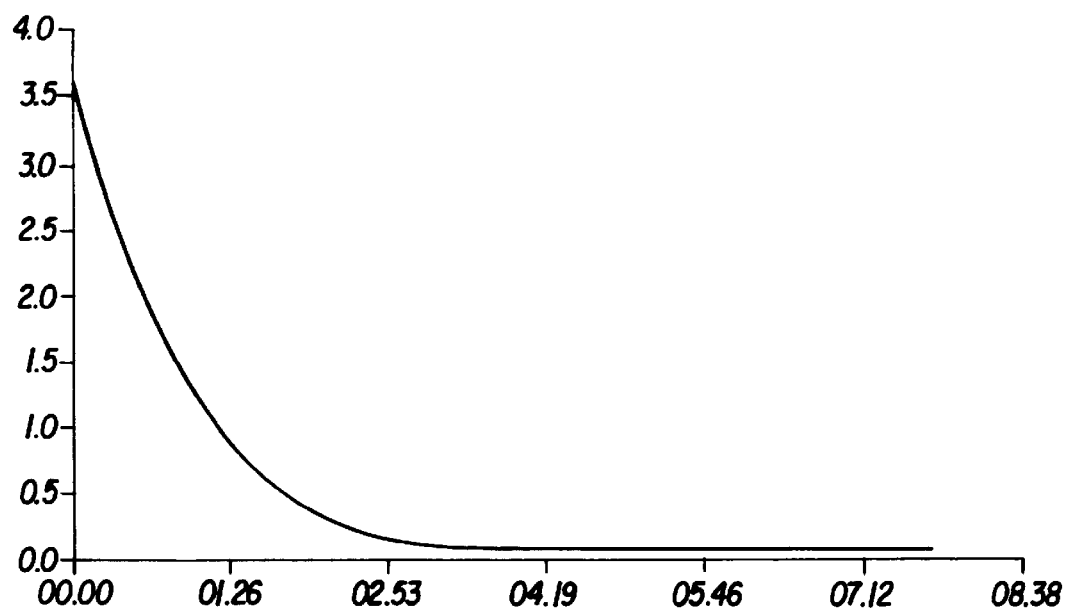
FIG. 4 illustrates test results using the present invention for Doddington sandstone.
Figure 5:
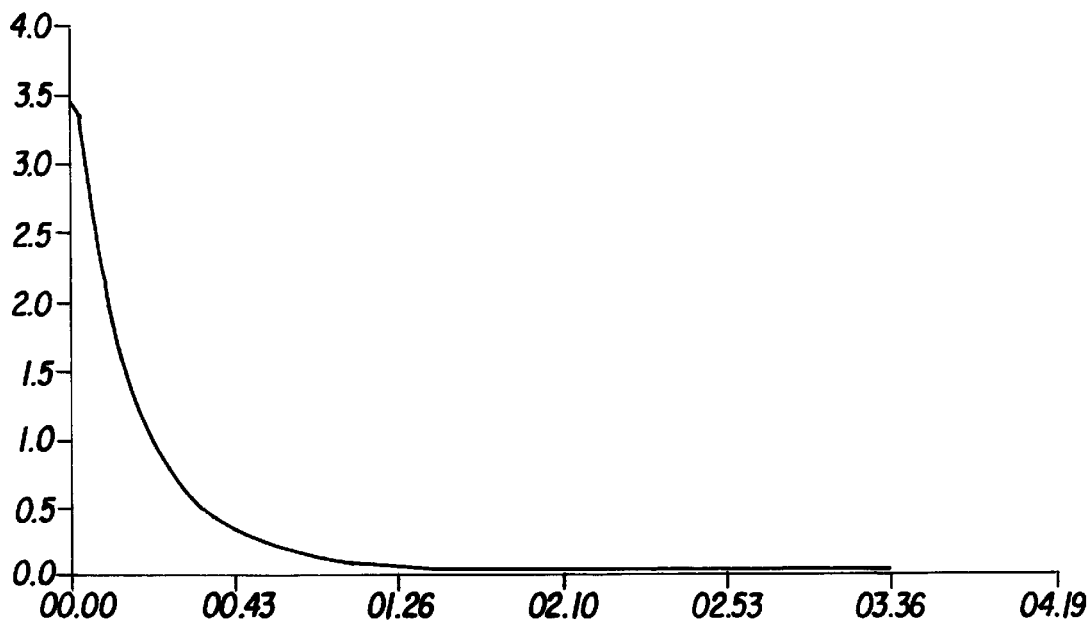
FIG. 5 illustrates test results utilizing the present invention for Sprintwell sandstone.
Figure 6:
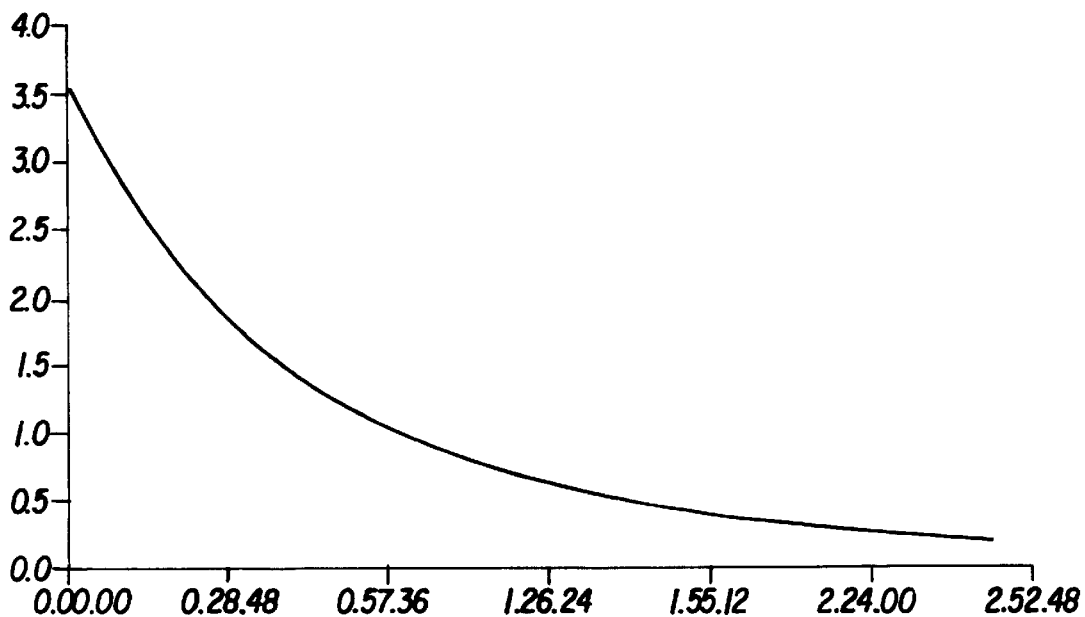
FIG. 6 illustrates test results utilizing the present invention with clay.

Preliminary tests were carried out with disks containing sandstone and clay cuttings which were then inserted in the measurement device and fluxed with gaseous nitrogen; the results are given in FIGS. 4, 5 and 6 for Doddington sandstone, Sprintwell sandstone and clay respectively, the curves of which on the graphs show the time (in hours, minutes and seconds on the abscissa) needed to dissipate a pressure difference of 3.5 bar (on the ordinate) applied between the two faces of each disk of cuttings.

Figure 7:
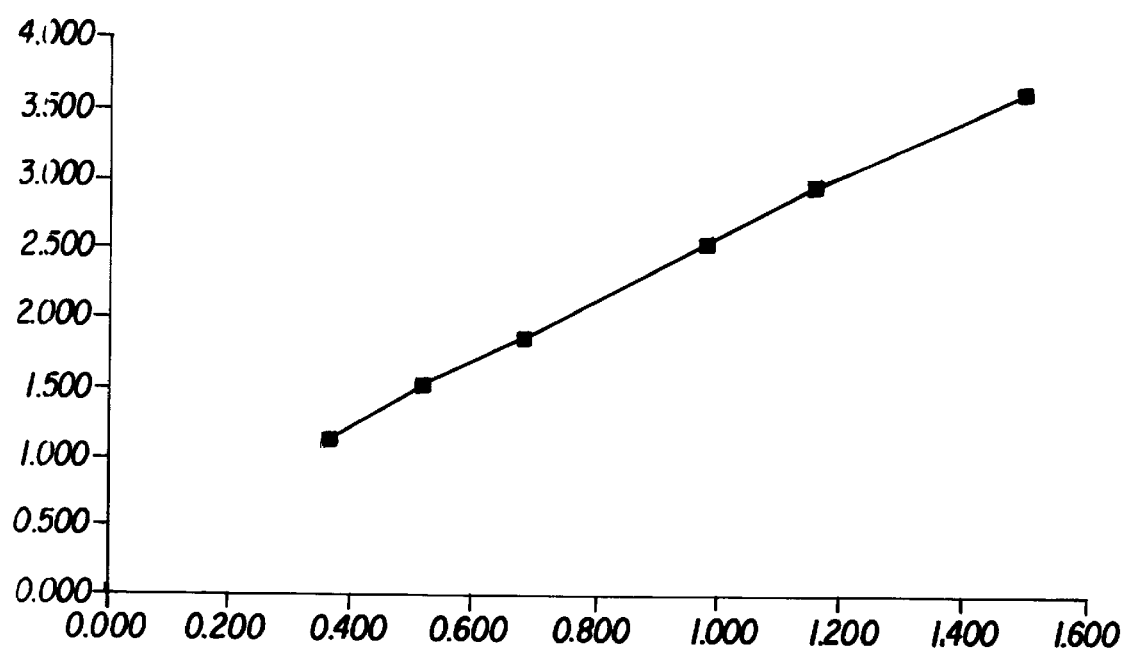
FIG. 7 illustrates pressure versus flow rate utilizing the present invention.

FIG. 7, on the other hand, shows a pressure against (on the ordinate expressed in bar) flow rate graph (on the abscissa expressed in cc/min.) for stationary flow through the disk containing clay cuttings.

The next step was to check whether the permeability values, obtained using the device object of this invention, were consistent with those measured using the traditional method on a test core.

For this, three ceramic samples of known and certified permeability (1 mD, 5 mD and 50 mD) were employed on which permeability was measured on test cores using the traditional method; at the same time, the samples were crushed to obtain "synthetic" cuttings on which permeability was measured using the measuring device object of this invention obtaining results that fell within the limits of experimental error.

Further tests were carried out on sandstone test cores coming from the rock reservoir of an oil well; permeability was measured using the steady state method on samples taken from the cores and characterised by very wide ranging degrees of permeability (from tenths of an mD to greater than 500 mD).

Afterwards, "synthetic" cuttings were obtained by crushing and permeability was measured using the device object of this invention.

The permeability measurements obtained on these cuttings were substantially the same as those obtained on the core (Table 1).

Finally, then, the method described here adds to and improves on existing known methods in a completely unexpected way and can be used as an industrial instrument for a campaign of on site measurements.

The costs of measuring permeability are quite low because of the availability of cuttings during drilling and also because the method can form part of a package of on site measurements on cuttings: acoustic, mechanical and petrophysical measurements.

TABLE 1

| CORE (mD) | CUTTINGS (mD) |
|---|---|
| 520 | 540 |
| 190 | 190 |
| 64 | 62 |
| 20 | 25 |
| 103 | 64 |
| 270 | 235 |
| 28 | 9.3 |
| 11 | 6.2 |

We claim:

1. A device used for the direct measurement of the permeability of rock fragments coming directly from the drilling of an oil well, commonly called cuttings which have dimensions less than one centimeter, said device consisting of a hollow cylindrical body (c) that presents an inlet hole for receiving fluids (i), surfaces defining said hole having threads (h) for receiving a closing plug having threads (h') for engaging threads (h) and a hydraulic seal (g) in which is placed a sample holder disk (d) which rests on the seal (g) and is overlapped by a porous sintered steel septum (e) on which a closing plug (f) is situated with an outlet hole for the passage of fluids (i'), the closing plug is suitable to allow the closure of the hole on the cylindrical body (c), the sample holder disk (d) consists of a resin (b) in which cuttings (a) are encapsulated, which presents flat, parallel faces with the two surfaces of each encapsulated cutting exposed on each side.

2. The device according to claim 1, wherein the material of the body (c) and the plug (f) is steel or plexiglass.

3. The device, according to claim 1, wherein the seals are O-rings.

4. The device of claim 1 wherein the sample holder disk, is characterized by the fact that the resin (b) is selected from the group consisting of epoxy, polyurethane and acrylic resins.

5. A method for the direct measurement of the permeability of rock fragments coming directly from the drilling of an oil well employing the device, according to claim 1, comprising, providing a pressure difference between the two faces of the disk (d); measuring said pressure difference on the two faces of the disk (d) and measuring the flow rate of the fluid.

6. A steady or non steady state method for the direct measurement of the permeability, according to claim 5.

7. The device according to claim 1 wherein the fluid is water or gaseous nitrogen.

8. The device according to claim 1, further comprising a pump (a) that provides a pressure difference between the two faces of the disk; a manometer (p) for measuring said pressure difference and a flowmeter (y) for measuring the flow rate of the fluid.

* * * * *